United States Patent
Serina et al.

(10) Patent No.: US 6,935,158 B2
(45) Date of Patent: Aug. 30, 2005

(54) MIS HYDROGEN SENSORS

(75) Inventors: Flaminia Serina, Grosse Pointe Farms, MI (US); Gregory W. Auner, Livonia, MI (US); Ka Yuen Simon Ng, West Bloomfield, MI (US); Ratna Naik, Ann Arbor, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 10/472,988

(22) PCT Filed: Mar. 16, 2001

(86) PCT No.: PCT/US01/08313

§ 371 (c)(1),
(2), (4) Date: Mar. 15, 2004

(87) PCT Pub. No.: WO01/69228

PCT Pub. Date: Sep. 20, 2001

(65) Prior Publication Data

US 2005/0074970 A1 Apr. 7, 2005

Related U.S. Application Data

(60) Provisional application No. 60/198,843, filed on Apr. 21, 2000, and provisional application No. 60/190,369, filed on Mar. 17, 2000.

(51) Int. Cl.[7] .............................................. H01L 41/08

(52) U.S. Cl. .................... 73/31.05; 73/24.01; 73/24.04; 73/24.06; 73/31.01; 73/31.06

(58) Field of Search .............................. 438/14, 16, 17, 438/18; 73/31.05, 23.2, 23.31, 24.01, 24.04, 24.06, 31.01, 31.06

(56) References Cited

U.S. PATENT DOCUMENTS 5,698,771 A * 12/1997 Shields et al. ............. 73/31.05

* cited by examiner

Primary Examiner—David Nelms
Assistant Examiner—Renee R. Berry
(74) Attorney, Agent, or Firm—Rohm & Monsanto, PLC

(57) ABSTRACT

Hydrogen gas sensors employ an epitaxial layer of the thermodynamically stable form of aluminum nitride (AlN) as the "insulator" in an MIS structure having a thin metal gate electrode suitable for catalytic dissociate of hydrogen, such as palladium, on a semiconductor substrate. The AlN is deposited by a low temperature technique known as Plasma Source Molecular Beam Epitaxy (PSMBE). When silicon (Si) is used the semiconducting substrate, the electrical behavior of the device is that of a normal nonlinear MIS capacitor. When a silicon carbide (SiC) is used, the electrical behavior of the device is that of a rectifying diode. Preferred structures are Pd/AlN/Si and Pd/AlN/SiC wherein the SiC is preferably 6H—SiC.

6 Claims, 12 Drawing Sheets

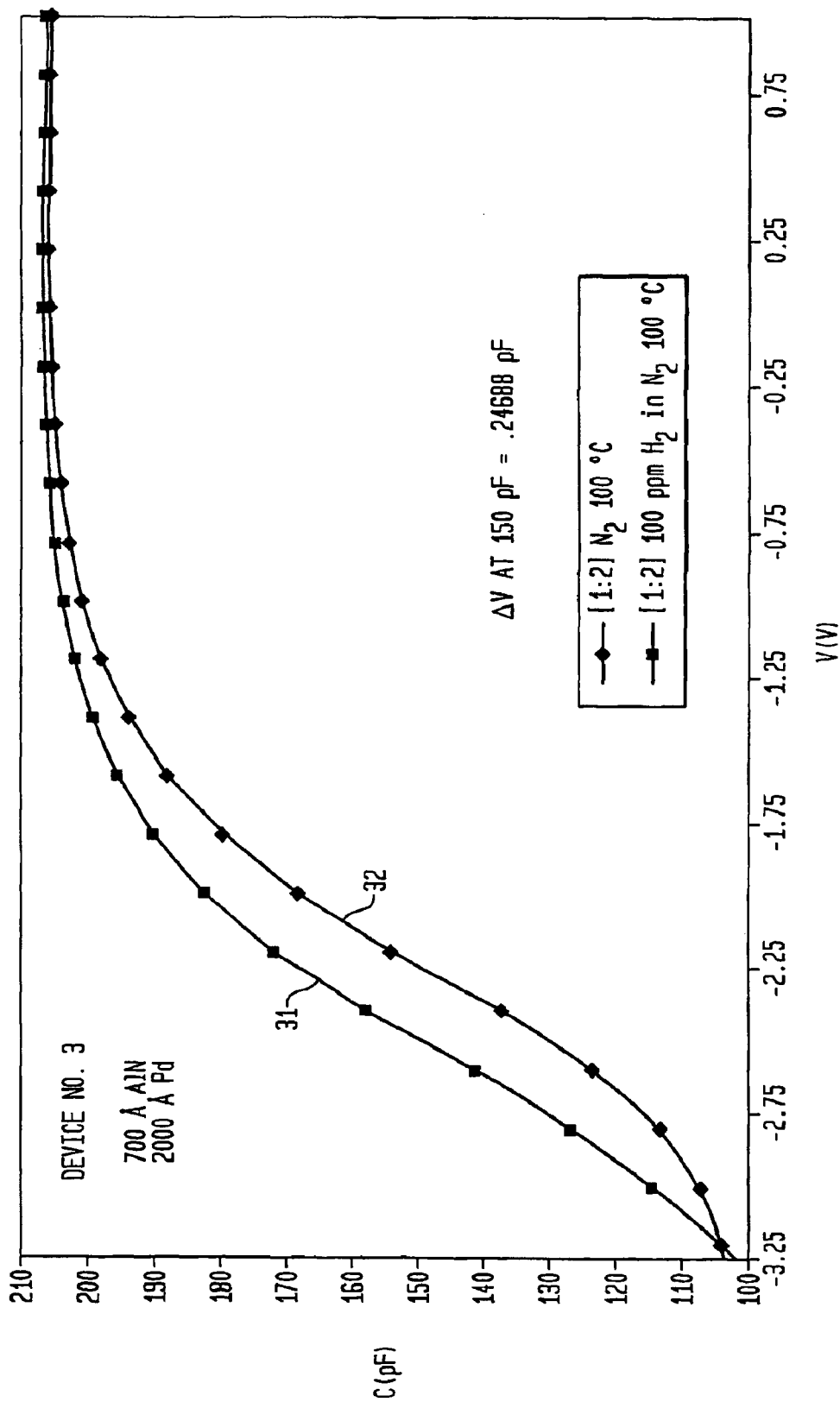

MIS HYDROGEN SENSORS

CROSS REFERENCE TO RELATED APPLICATIONS

This application is a continuation of, and claims the benefit of, provisional application No. 60/190,369 filed on Mar. 17, 2000 and provisional patent application No. 60/198,843 filed on Apr. 21, 2000.

BACKGROUND OF THE INVENTION

1. Field of the Invention

This invention relates generally to gas sensors, and more particularly, to solid state sensors that can selectively detect the presence of hydrogen.

2. Description of the Related Art

A device that can detect the concentration of hydrogen in the presence of other gases would have multiple uses in, inter alia, the transportation industry. For example, in the space program, a mass spectrometer is employed to detect the presence of hydrogen in and around the space shuttle. This known device suffers from the disadvantage that, while it can detect the presence of hydrogen, it is incapable of identifying the source, or location of hydrogen leakage. There is therefore, a need for small, relatively inexpensive sensors, that can be placed in multiple locations for detecting a source of hydrogen gas emission.

As another example, the automotive industry has been developing new power sources, such as a hydrogen combustion engine and a hydrogen fuel cell. The safe use of these new power sources will require hydrogen sensors that can operate over a broad range of temperatures, pressures, and gas compositions.

Although there has been some effort expended to develop hydrogen sensors in the past, most, if not all, known hydrogen sensors have not entered commercial production because they have failed to meet all of the required parameters. Hydrogen can be detected readily in an environment that contains only hydrogen. However, it is considerably more difficult, with current technology, to detect hydrogen when it is mixed with other gases. Furthermore, with current technology, if a sensor is optimized to overcome the selectivity problem, temperature and pressure requirements are not satisfied. There is a need, therefore, for a sensor that overcomes all the present problems of selectivity, temperature, and pressure, whereby the sensor would be made usable in a realistic environment.

It is known that catalytic metals can be used as gates for gas sensitive field effect devices, such as transistors, capacitors, diodes, and the like. Known devices include metal-insulator-semiconductor (MIS) or metal-oxide-semiconductor (MOS) structures. Gas sensitivity occurs because reaction intermediaries give rise to electrical phenomena at the metal-insulator or metal-semiconductor boundaries. In a hydrogen sensor, for example, molecular hydrogen dissociates at the catalytic metal electrode surface and the hydrogen atoms produced diffuse through the electrode and are adsorbed at the electrode/insulator interface. The dipole moment of the adsorbed atoms produce a detectable change in threshold voltage of the device, thereby giving an indicate of the concentration of hydrogen in the gas to which the device is exposed.

The prior art has determined that palladium is the ideal catalyst for hydrogen diffusion. Hydrogen travel time within a palladium thin film is sufficiently small for this catalyst to be used as a selective "membrane." Palladium (Pd) may provide acceptable selectivity, but when pure Pd films are used, other problems are typically encountered. For example, below 300° C., Pd undergoes an a-b phase transformation in the presence of a high concentration of hydrogen. Also, contraction and expansion of a Pd film leads to embrittlement and eventual fracture of the metal.

To overcome these problems, the prior art has suggested using Pd in combination with other materials. In particular, the prior art has explored the use of Pd/Ni alloy and Pd/Group V/Pd membranes. However, such membranes have exhibited temperature range limitations. For example, if these known devices are used at high temperatures, the membrane layers will melt into each other, preventing hydrogen from diffusing therethrough. Moreover, electron beam evaporation is used in the construction of the known alloys, requiring a substrate that also melts if used at high temperatures. In one effort to overcome these temperature limitations, a polycrystalline diamond film was applied over a Pd thin film by plasma-enhanced chemical vapor deposition. The temperature problem was not overcome since this device was useful only to 200° C.

It is additionally a problem that palladium is a good catalyst for many reactions, and therefore, poisoning occurs on the palladium surface. By "poisoning," it is meant that other gases also adsorb at the palladium surface, closing the pores necessary for the diffusion of hydrogen. Some of the many adverse gases in this scenario are oxygen ($O_2$), and particularly carbon monoxide (CO). The presence of $O_2$ at the Pd surface results in dissociation into single oxygen atoms, which then react in the presence of hydrogen ions to form water. Fortunately, the water evaporates and frees the Pd sites. In fact, in order to purge palladium films from hydrogen, a flow of oxygen gas is supplied on the surface of the device, and vice versa, to purge a Pd film from oxygen poisoning, hydrogen gas is used. On the other hand, on a Pd surface, CO does not react easily with other elements, and therefore, CO poisoning is a significant problem in the art.

There is, therefore, a need for a hydrogen sensor that can operate over extended ranges of temperature and pressure, and in the presence of multiple gases and contaminants.

SUMMARY OF THE INVENTION

The foregoing needs and other objects are achieved by this invention which provides, in a first device embodiment, a semiconductor device, that can be used, in a preferred embodiment, as a hydrogen sensor. More-specifically, the hydrogen sensor of the present invention is an MIS device that differs from previously developed MIS devices, by employing aluminum nitride (AlN) as the insulator in the MIS structure. AlN is a wide bandgap (~6.2 EV) semiconductor, found to be chemically stable and to have the capability of withstanding high temperatures. In MIS sensors, a catalytic film (i.e., one which dissociates molecules) is separated from a semiconductor film by a dielectric film. Exposure to a gas, e.g., hydrogen, changes the capacitance of the sensor. The change in capacitance can then be measured as an indication of gas concentration.

In a broad device embodiment of the present invention, a sensor for the detection of hydrogen gas comprises a semiconductor substrate; an epitaxial layer of AlN disposed on a face surface of the semiconductor substrate as an insulating layer; and a metal electrode disposed on the insulating layer, the metal electrode being a catalyst for hydrogen diffusion.

Of course, the choice of catalytic metal for the electrode will depend on the particular chemical substance being detected. The use of rhodium, for example, would enable the detection of nitric oxide. The use of the MIS device to detect hydrogen is intended to be illustrative, and not limiting. Examples of suitable metals known to be useful in detecting chemical species include, but are not limited to Pt, Pd, Ir, Rh, Ru, Os, Fe, Ag, Au, Cu, and Ni, either alone or alloyed with each other. It is also within the contemplation of the invention that the catalytic metals can be alloyed with non-catalytic metals, or insulators, to increase the active surface area of the catalyst and to prevent surface poisoning as is known in the art. Since the catalytic metal electrode operates as a "selective membrane" for the chemical species to be detected, any combination of materials known or developed, that can selectively detect a chemical species, is within the contemplation of the present invention.

In the preferred hydrogen sensor embodiment described in detail herein, the preferred catalytic metals include Pd, Pt, Rh, and alloys thereof, and most preferably Pd. The catalytic metal electrode layer in the device of the preferred embodiment is typically a thin film of pure Pd ranging in thickness from about 1000 Å to 1 micron, and most preferably about 1000 Å to 2000 Å.

The semiconductor substrate is a semiconductor material of one conductivity type (doped p- or n-type). Typically, the semiconductor substrate is a silicon (Si) wafer or silicon carbide (SiC) wafer. The semiconductor substrate material affects the operation of the device as will be described in detail hereinbelow. Silicon carbide, and particularly 6H—SiC, is especially useful in high temperature embodiments.

The insulating aluminum nitride layer is an epitaxial layer of AlN (the thermodynamically stable wurtzite form). In a preferred embodiment, the epitaxal layer of AlN is grown by a Plasma Source Molecular Beam Epitaxy (PSMBE) technique that is described in detail in International Publication WO 00/61839 published on Oct. 19, 2000, the text of which is incorporated herein by reference. In preferred embodiments, the insulating AlN layer has a thickness of between about 500 Å to 5000 Å, and preferably about 1000 Å.

In one preferred embodiment of the invention, silicon is the substrate for a Pd/AlN/Si MIS hydrogen sensor. In a specific illustrative embodiment, the Si substrate is an n-type (111)-oriented wafer. The insulating aluminum nitride layer is an epitaxial layer of AlN deposited by PSMBE and the gate layer is a thin film of Pd that may be deposited on the AlN film in any known manner, illustratively by magnetron sputtering through a hard mask.

In a second preferred embodiment of the invention, silicon carbide (SiC), and preferably n-type 6H—SiC, is the substrate for a device having the structure Pd/AlN/SiC. Although both embodiments have an MIS structure, and are capable of selectively detecting hydrogen, the silicon carbide-based device has a different electrical characteristic than the Pd/AlN/Si device. The Pd/AlN/Si device responds to the presence of hydrogen by a shift in its ac capacitance versus bias voltage characteristic, similar to known MOS devices, whereas the Pd/AlN/SiC device responds by a shift in its forward I(V) characteristic, similar to a rectifying diode.

Of course, multilayered devices having additional layers of metals and/or semiconductors are within the contemplation of the invention. For example, a layer of a Group VB metal, such as zirconium, can be interposed between the insulating layer and the palladium gate electrode, by standard deposition techniques. The sensors may be also be fabricated to incorporate additional features, such as a built-in heating coil, may be micromachined for industrial applications.

The gas-sensitive MIS field effect transistor structures are described herein by way of example. It is to be understood that the invention can encompass other electrical devices that can be devised including, for example, varieties of field effect transistor (FET) structures other than the examples described herein, MIS diodes and transistors, Schottky barrier devices, electrochemical cells, surface acoustic wave devices, piezo-electric crystal oscillators and chemoresistive devices.

In a method of embodiment of the present invention, the AlN insulating layer is epitaxially deposited on a first surface of a semiconductor substrate and a layer of catalytic metal is deposited on the epitaxial layer of AlN by any known technique, such as by sputtering. In a particularly preferred method embodiment of the present invention, the AlN layer is deposited by PSMBE, and more specifically by forming a plasma of high energy activated aluminum ions and activated nitrogen ion species by the application of rf power to a source of aluminum and nitrogen so as to create a low energy flux of plasma; exposing the semiconductor substrate to a low energy flux of the plasma so as to deposit an epitaxial layer of AlN film on the exposed face of the substrate. In specific preferred embodiments, the PSMBE is conducted at a temperature in the range of 300° C.–900° C. and the rf power applied to create the plasma is between about 100 W–300 W. PSMBE deposits a thermodynamically stable, wurtzite AlN layer, epitaxially oriented on the substrate, to any desired thickness, illustratively, between about 500 Å to 5000 Å.

BRIEF DESCRIPTION OF THE DRAWING

Comprehension of the invention is facilitated by reading the following detailed description, in conjunction with the annexed drawing, in which:

FIG. 4 is an exemplary graphical representation of the capacitance-voltage response of an MIS sensor in accordance with the present invention to the presence of hydrogen;

in FIG. 6, 100° C. in FIG. 7, and 130° C. is FIG. 8;

DETAILED DESCRIPTION OF THE INVENTION

Figure 1:
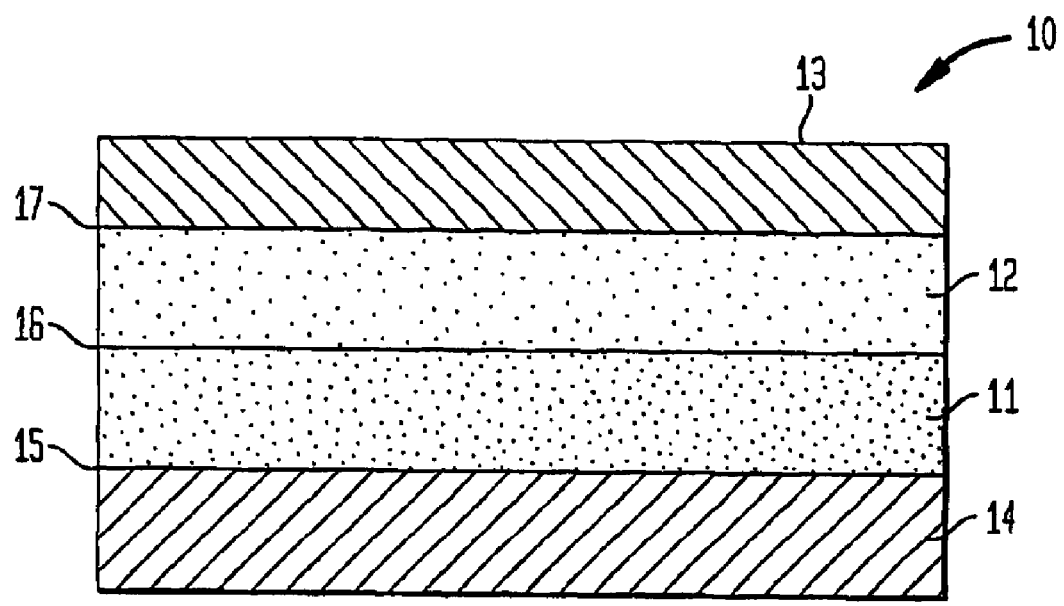
FIG. 1 is a schematic representation of an experimental sensor constructed in accordance with the principles of the invention.

FIG. 1 is a schematic representation of an illustrative embodiment of the present invention which is metal-insulator-semiconductor (MIS) hydrogen sensor 10. The semiconductor substrate 11 is shown to have an ohmic contact 14 on a back surface 15, and an insulating layer 12 on a front face surface 16. A metal electrode 13 is disposed on the face surface 17 of insulating layer 12. Insulating layer 12 is a thin film of AlN, and preferably AlN that has been deposited via PSMBE so as to ensure epitaxial growth of the AlN film.

In one embodiment, hydrogen sensor 10 has a silicon substrate. In an alternative embodiment, hydrogen sensor 10 has an silicon carbide substrate, specifically 6H—SiC. The silicon carbide-based sensors were designed to ensure functionality at higher temperatures than the Si-based devices, covering a broad range from room temperature up to 500° C. Further, while it is important to use the low temperature PSMBE technique to deposit an epitaxial layer of AlN on a silicon substrate, devices can be fabricated on SiC substrates by higher temperature processes, such chemical vapor deposition (CVD), plasma-assisted CVD, metal organic CVD, and the like. Nevertheless, in a preferred embodiment of the invention, the silicon carbide-based sensor is fabricated by the PSMBE technique.

In a method embodiment of the present invention, the thin AlN film is formed by exposing a heated substrate to a low energy flux of target atoms in an ultrahigh vacuum PSMBE system. The PSMBE system, which is described in detail in International Publication WO 00/61839 published on Oct. 19, 2000, uses a plasma deposition source which is a magnetically-enhanced, generally cylindrical hollow chamber comprising a cathode. The chamber is lined with the target material which, in the present case, is MBE-grade aluminum. The target material is milled so that its thickness is greater at the upper, or exit, end of the chamber than the thickness at the lower end. Illustratively, the chamber has about a 3° internal taper. Process gases, specifically argon and nitrogen, are introduced into the plasma deposition source. A plasma of high-energy aluminum, nitrogen, and argon species is formed in the chamber by the application of dc or rf power to the source. In this case, the application of rf power, particularly rf power between 110 W and 300 W, produces an epitaxial layer of the desired thermodynamically stable (wurtzite) AlN on the semiconductor substrate. The application of pulsed dc power to the source will result in the epitaxial deposition of the metastable cubic (zinc-blende) AlN. A magnetic field and the taper of the interior of the cathode cooperate to confine the plasma to the cathode.

The low energy flux of target atoms is extracted from the exit end of the chamber either by the action of an impeller rotatably mounted in the cathode source or by an acceleration bias applied to the substrate.

In this manner, a film is formed on a front face surface of the heated substrate. Films having a thickness of at least 500 Å have been produced by this method. Thickness, of course, is a function of deposition time, and films ranging from 10 Å to several microns, are possible by the PSMBE method.

The thermodynamically stable wurtzite form of AlN and the metastable zinc-blend form may be fabricated selectably in the same PSMBE system by varying the process conditions as illustratively set forth in Table 1. Of course, in addition to AlN, and other Group III-V semiconductors, and their alloys, the PSMBE system can be adapted to fabricate semiconductor devices from other elements, and to form multilayered heterostructure devices of varying composition. The system can readily be adapted, as is known in the art, to include a source of donor or acceptor electrons to form p-n junction devices.

TABLE 1

| Parameter | Hexagonal (wurtzite) AlN | Cubic (Zinc-Blende) AlN |
|---|---|---|
| Dynamic Gas Pressure | 1–10 mTorr | 1–10 mTorr |
| Argon Flow | 20–40 sccm | 20–40 sccm |
| Nitrogen Flow | 20–40 sccm | 2–40 sccm |
| Substrate Temperature | 300° C.–900° C. | 300° C.–800° C. |
| rf Power (to source) | 100 W–300 W | 0 |
| Pulsed dc Power | 0 | 100 W–300 W |
| Acceleration Bias (to substrate) | 12 V–15 V (neg.) | 0–15 V (neg.) |
| Substrates | Si(111), Al$_2$O$_3$ (R-plane), Al$_2$O$_3$ (C-plane), 6H-SiC | Si(100), 3C-SiC, and MgO(100), or combinations thereof |

Of course, the semiconductor substrate may be pre-treated, in accordance with known techniques, such as by subjecting the substrate to solvents to de-grease it and to remove surface oxidation, or by pre-heating.

The metal electrode may be deposited on the face surface of the insulating AlN layer by any known technique, illustratively sputtering through a hard mask. The thickness of the metal electrode layer is typically between about 1000 Å to 1 micron. In the preferred MIS hydrogen sensor embodiments, the metal layer is palladium having a thickness between about 1000 Å and 2000 Å.

The ohmic contact, on the back surface of the semiconductor substrate, may be any suitable conductive metal, and can be deposited by any known technique, such as sputtering. In the specific embodiments described herein, the contact layer is a sputtered aluminum film for the Si-based device and a platinum film for the SiC-based device. The finished device may be heated, or annealed, as is known in the art.

EXAMPLE 1

In a particular illustrative embodiment, Pd/AlN/Si MIS hydrogen sensor devices were fabricated by PSMBE in order to assure epitaxial growth of the insulating AlN layer. The Si substrate was silicon<111>N-type with specified low resistivity, and a thickness of about 380±20 mm.

The base pressure of the ultrahigh vacuum PSMBE system was $7.3 \times 10^{-9}$ TORR, and during deposition, the dynamic pressure was maintained constant at $3.5 \times 10^{-3}$ TORR. The process gases were maintained at a constant flow of 40 sccm of argon (Ar) and 10 sccm of nitrogen (N$_2$). The substrate temperature was kept constant at 650° C. during the entire 10 hour period required to deposit AlN on the substrate to the desired thickness. An acceleration bias of 10 eV was applied to the substrate.

Optical null ellipsometry of the AlN substrate on the Si<111>substrate measured the thickness of the AlN layer and the index of refraction. Devices having different AlN layer thicknesses of (e.g., 700 Å and 1200 Å) were characterized and the results are set forth hereinbelow.

Figure 2A:
FIG. 2A shows Reflection High Energy Electron Diffraction (RHEED) high energy electron diffraction images of for Si<111>at 90° before deposition of AlN and FIG. 2B shows the images obtained after deposition of AlN on the substrate.
Figure 2B:
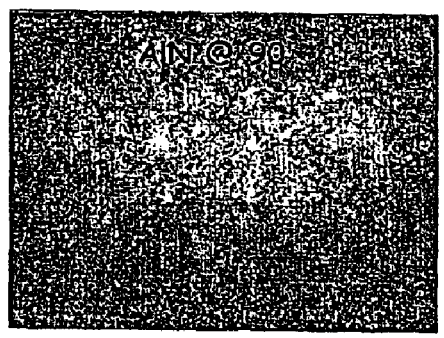
Figure 3A:
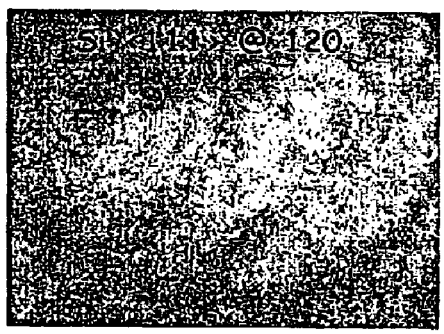
FIG. 3A shows RHEED images of for Si<111>at 120° before deposition of AlN and FIG. 3B shows the images obtained after deposition of AlN on the substrate.
Figure 3B:
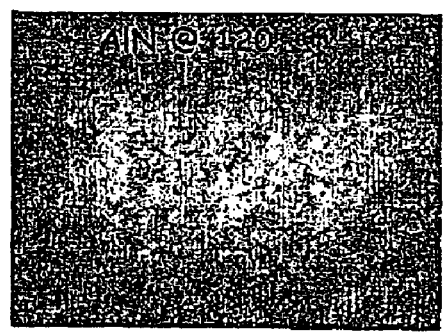

FIG. 2A and FIG. 2B shows Reflection High Energy Electron Diffraction (RHEED) images for Si<111>and AlN at 90°, and FIG. 3A and FIG. 3B shows RHEED-type high energy electron diffraction images for Si<111>and AlN at 120°. The images of FIG. 2A and FIG. 3A were obtained before deposition of AlN on the substrate and the images of FIG. 2B and FIG. 3B were obtained after deposition of AlN. FIGS. 2 and 3 confirm the epitaxial growth of AlN film.

A palladium layer was deposited on top of the epitaxial AlN film, through a hard mask, via a magnetron sputtering technique, with a base pressure of $3.37 \times 10^{-6}$ TORR and a dynamic pressure of $1.95 \times 10^{-4}$ TORR. A Tencor P-4 long scan profiler was used to measure layer thickness of the Pd layer. The back ohmic contact, which was an Al film having, in this embodiment, a thickness of 1500 Å was deposited by sputtering.

EXAMPLE 2

In a second specific illustrative embodiment, a Pd/ALN/SiC MIS hydrogen sensor (see, Table 2, Device No. 5) was fabricated by depositing an epitaxial layer of AlN on a standard n-type 6H—SiC wafer by PSMBE under process conditions described above in Example 1. RHEED images (not shown) were obtained before and after the deposition of the AlN on the 6H—SiC wafer to insure epitaxial growth. In this specific embodiment, the epitaxial layer of AlN was 1600 Å thick. A Pd gate layer was deposited on the SiC-based structure to a thickness of 1000 Å. The back contact to the semiconductor substrate, in the SiC-based embodiment, was Pt sputtered to a thickness of 1500 Å.

Table 2 summarizes the devices fabricated in accordance with Examples 1 and 2:

TABLE 2

TABLE 1: INSULATOR AND CATALYST THICKNESS

| Device | Substrate | AlN Thickness (Å) | Pd Thickness (Å) |
|---|---|---|---|
| 1 | Si <111> | 700 | 1000 |
| 2 | Si <111> | 1200 | 1000 |
| 3 | Si <111> | 700 | 2000 |
| 4 | Si <111> | 1200 | 2000 |
| 5 | 6H-SiC | 1600 | 1000 |

Experimental Results:

The tests required for electrical characterization of the devices were conducted in a testing chamber that was surrounded with a protective flow of N$_2$ to ensure constant boundary conditions of the system. All the experiments were run at ambient pressure to stimulate practical application scenarios. The testing chamber contained a resistive ceramic heater to allow for testing at various temperatures. Direct current (dc), at different voltages, was applied to the heating coils in the ceramic heater, and the system was allowed to reach steady state before electrical testing was performed. The sensor to be tested was placed horizontally on a Pt foil tray placed on top of the ceramic heater. The Pt foil served to connect the back contact of the device to the electrical ground. A thermocouple attached to the foil monitored, and hence, regulated the temperature of the device being tested. A weighted Pt wire was lowered on the gate electrode of the device, thereby completing the circuit, and allowing measurements of capacitance, voltage, and current.

A data acquisition system with I/O ports controlled the flow and concentration of the various gases that were introduced into the chamber, and a manifold ensured proper mixing of the gases before they entered the chamber. The response of the device to the presence of hydrogen, alone or in the presence of other gases, was measured under controlled environmental scenarios, such as different temperature ranges and gas concentrations, which correspond to anticipated industrial applications.

The capacitance versus gate voltage curves, as well as the measurements of capacitance at constant bias, described below, were obtained using a computer-controlled Hewlett-Packard model impedance spectrometer at a probe frequency of 1 MHz.

FIG. 4 is a graphical representation of the capacitance-voltage (C-V) response of a Si-based sensor, of the type described in Example 1, when exposed to hydrogen. Referring to FIG. 4, capacitance, measured in picofarads (pF), is plotted on the vertical axis and voltage is plotted on the horizontal axis. Specifically, FIG. 4 shows the response of a Pd/AlN/Si hydrogen sensor (Table 2, Device No. 3) to hydrogen at 100° C. Curve 31 and was obtained in a constant flow of 100 sccm of N$_2$. Curve 32 shows a shift in the voltage axis when a constant flow of 100 sccm of 100 ppm H$_2$ in N$_2$ was substituted for the pure N$_2$. This shift is the basic output signal for this type of sensor. For the Si-based devices of Example 1, the C-V curves display the expected shape typical of parallel plate MIS capacitors biased in depletion (for n-type substrates, the gate voltage is negative with respect to the substrate).

Figure 5:
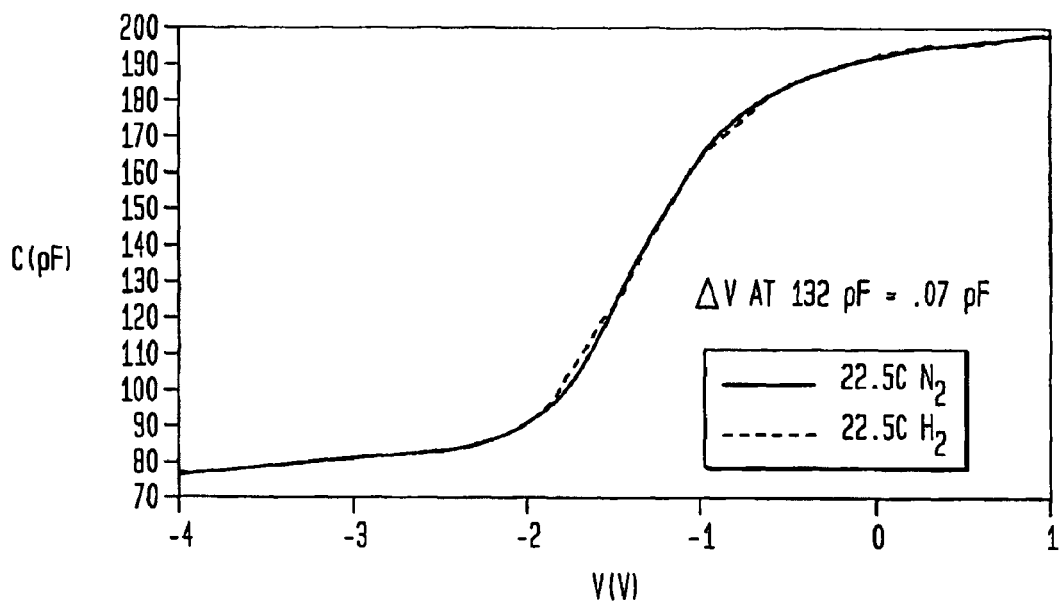
FIGS. 5–8 are graphical representations of the capacitance-voltage response of an MIS sensor in accordance with the present invention to the presence of hydrogen observed at various temperatures, specifically room temperature (22.5° C.) in FIG. 5, 50° C.
Figure 6:
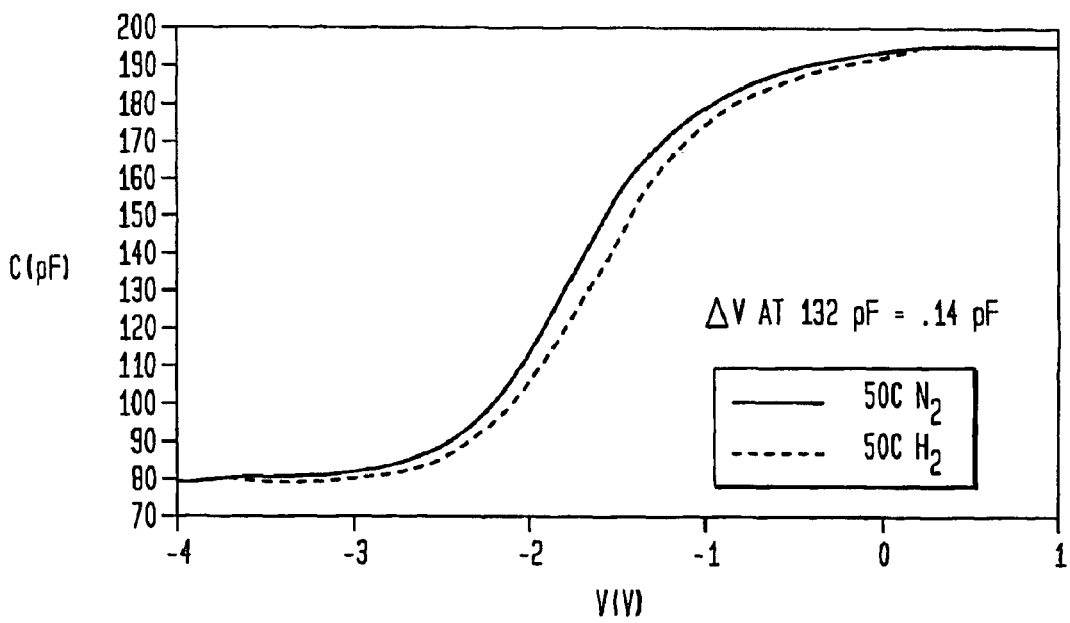
Figure 7:
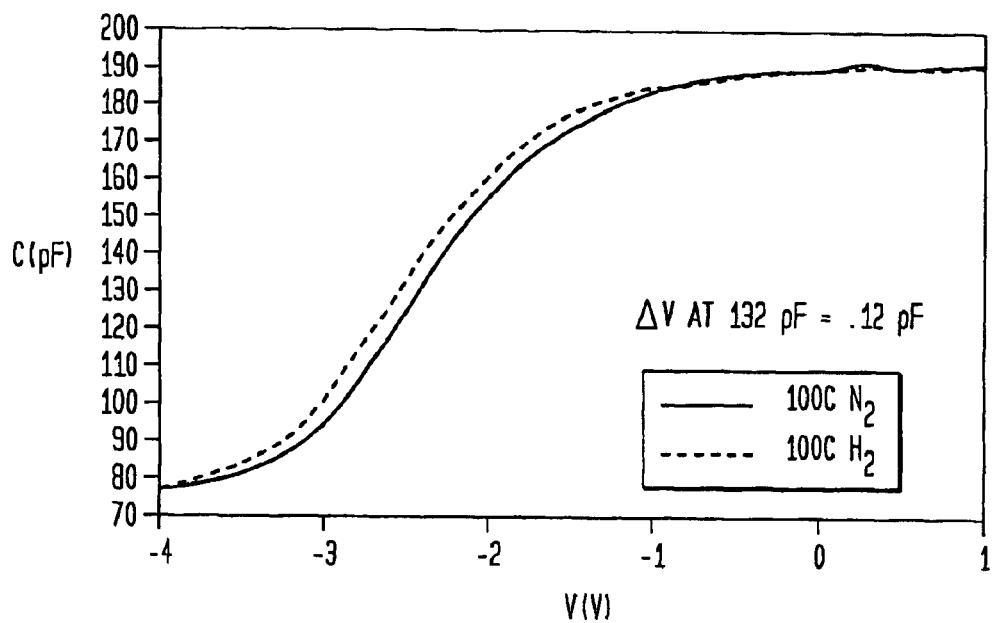
Figure 8:
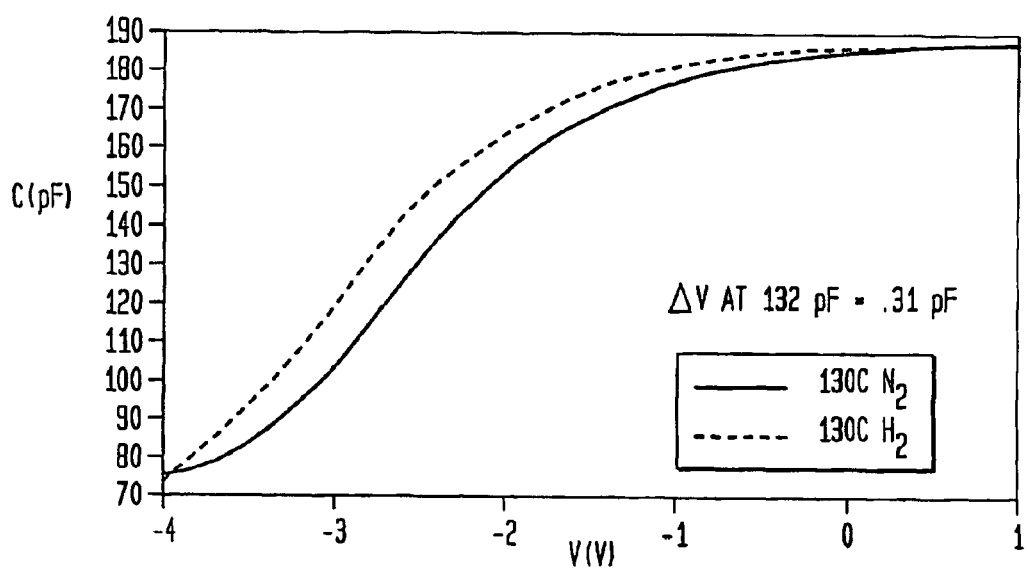

FIGS. 5–8 shows the C-V responses of another Pd/AlN/Si hydrogen sensor (Table 2, Device No. 1) to hydrogen (100 sccm of 100 ppm H$_2$ in N$_2$) at various temperatures, beginning with room temperature (22.5° C.) in FIG. 5 to 130° C. in FIG. 8. As shown in the graphs, the shift of the curve in the voltage axis is observable at all temperatures. Testing of devices with different AlN thickness demonstrated that a thinner insulator layer gives a larger response to hydrogen (see, FIG. 4 versus FIG. 7).

Figure 9:
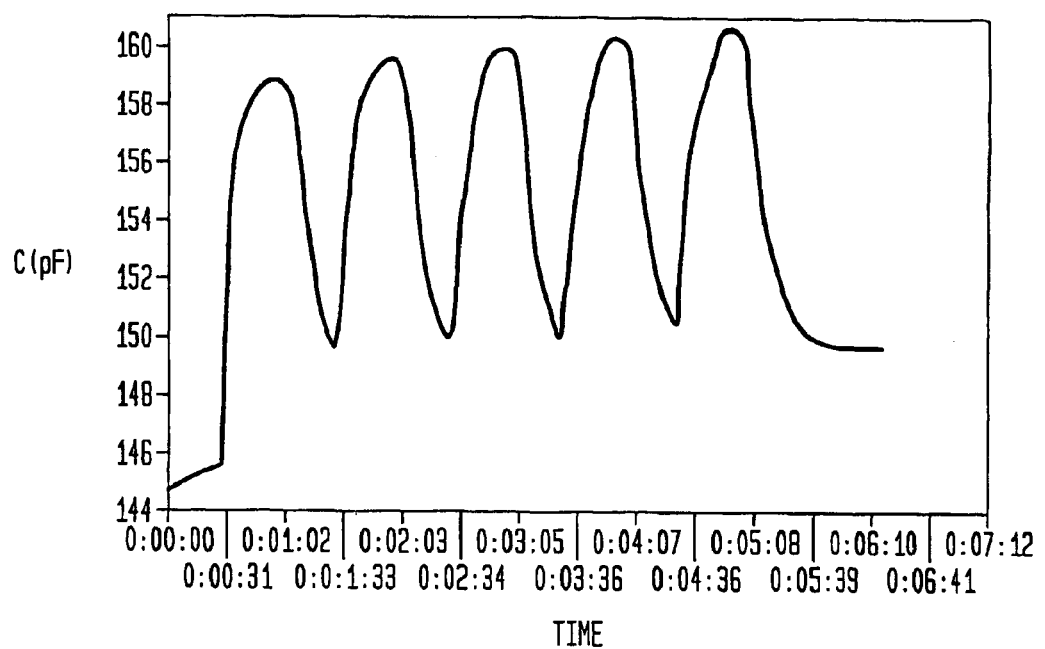
FIG. 9 is a graphical representation of the change in capacitance (pF) over time, measured in seconds, of an MIS sensor in response to periodic input of hydrogen into the gas stream.

In normal operation as a sensor, the device would be operated by either measuring the changes in its capacitance at constant gate voltage, or by using a feedback loop to keep constant capacitance and measuring the bias shift needed to maintain this capacitance in the presence of hydrogen. FIG. 9 is a graphical representation of the change in capacitance (pF) at constant gate voltage over time (sec) for a Pd/AlN/Si sensor (Table 2, Device 1) when subjected to a periodic (~every 30 seconds) change in gas composition impinging on the sensor from 100 sccm of pure nitrogen to 100 sccm of 100 ppm hydrogen in nitrogen at a constant temperature of 100° C. This data shows that the sensor rapidly responds to the presence of hydrogen.

Figure 10:
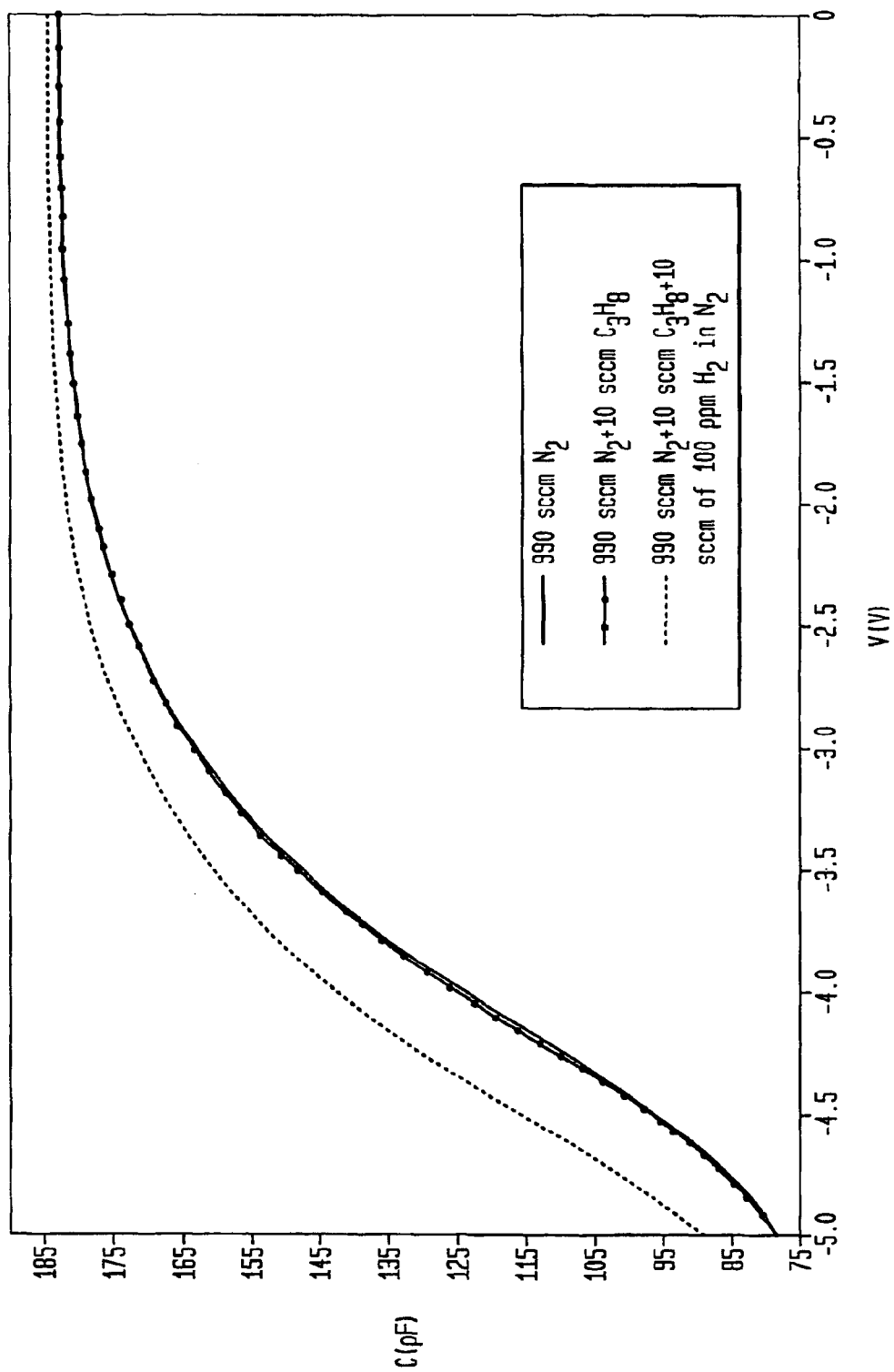
FIG. 10 is a graphical representation that shows the C-V response of a Pd/AlN/Si device to hydrogen in the presence of propane.

FIG. 10 is a graphical representation that shows the results that were achieved when the Pd/AlN/Si devices were tested in the presence of other gases, such as propane and oxygen. Referring to FIG. 10, curve 41 shows the response of Device No. 1 to 990 sccm N$_2$. Curve 42 is the response to 990 sccm N$_2$ and 10 sccm propane (C$_3$H$_8$). However, curve 43 shows a marked shift when H$_2$ is added to the mix, specifically 990 sccm N$_2$, 10 sccm C$_3$H$_8$, and 10 sccm H$_2$. Responses were also obtained in the presence of O$_2$ (not shown). Neither gas interfered with the detection of hydrogen, implying that the sensors are highly selective.

For completeness of the results, Table 3 represents the current versus voltage (I-V) response of a Pd/AlN/Si MIS sensor (Table 2, Device No. 4) at a constant temperature (121.5° C.). This table shows part of the data collected during I-V testing of the device, and by comparing the values at different currents, the shift is evident. Current is measured in microamps.

TABLE 3

DATA OF SENSOR #4 FROM I-V CHARACTERIZATION

| 100 ppm $N_2$ | | 100 ppm $H_2$ | |
|---|---|---|---|
| V | I | V | I |
| 6.00E−01 | 2.03E−05 | 6.00E−01 | 2.11E−05 |
| 6.50E−01 | 2.41E−05 | 6.50E−01 | 2.51E−05 |
| 7.00E−01 | 2.80E−05 | 7.00E−01 | 2.94E−05 |
| 7.50E−01 | 3.16E−05 | 7.50E−01 | 3.31E−05 |
| 8.00E−01 | 3.57E−05 | 8.00E−01 | 3.75E−05 |
| 8.50E−01 | 3.96E−05 | 8.50E−01 | 4.16E−05 |
| 9.00E−01 | 4.35E−05 | 9.00E−01 | 4.58E−05 |
| 9.50E−01 | 4.76E−05 | 9.50E−01 | 4.97E−05 |
| 1.00E+00 | 5.18E−05 | 1.00E+00 | 5.42E−05 |

From Table 3, it can be concluded that the Si-based MIS devices of the present invention have a higher response when capacitance measurements are used, although a shift is still present during I-V characterization.

The electrical behavior of the SiC-based embodiment of the present invention, on the other hand, is that of a rectifying diode, most likely a heterojunction diode with the AlN behaving as one of the semiconductors. The Pd/AlN/SiC sensor response is manifested by a marked shift in the forward current versus voltage characteristic of the device. For a fixed applied voltage, a convenient output variable for the SiC-based embodiment, is the shift in current due to the presence of hydrogen.

Figure 11A:
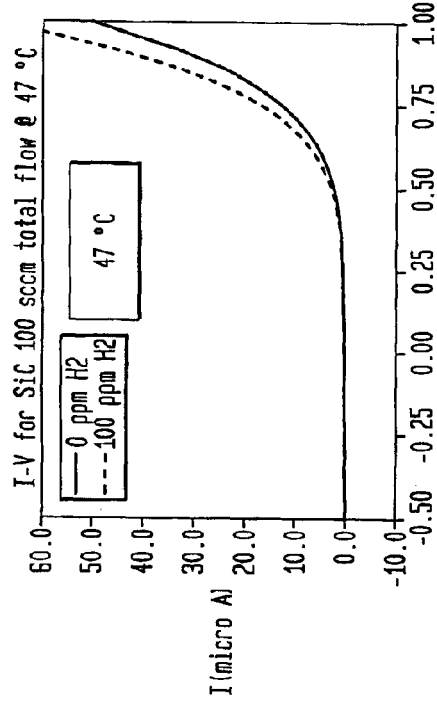
FIG. 11A–H are graphical representations of the current versus voltage (I-V) response of a silicon carbide-based device to the presence of hydrogen measured at constant temperatures ranging from room temperature to 283° C., and specifically on FIGS. 11A–H at 19° C., 47° C., 107° C., 130° C., 155° C., 211° C., 255° C., and 283° C., respectively.
Figure 11B:
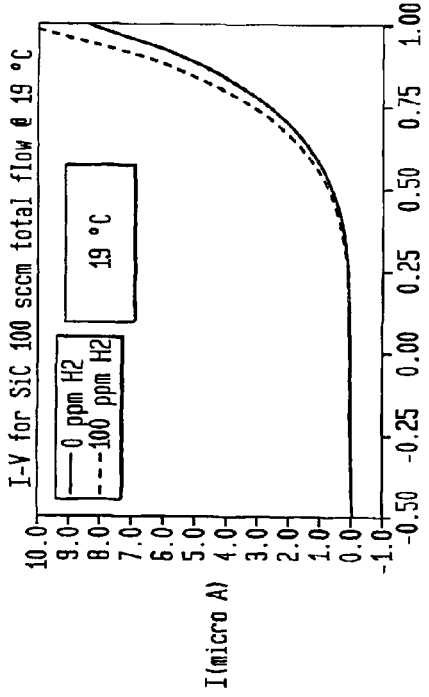
Figure 11C:
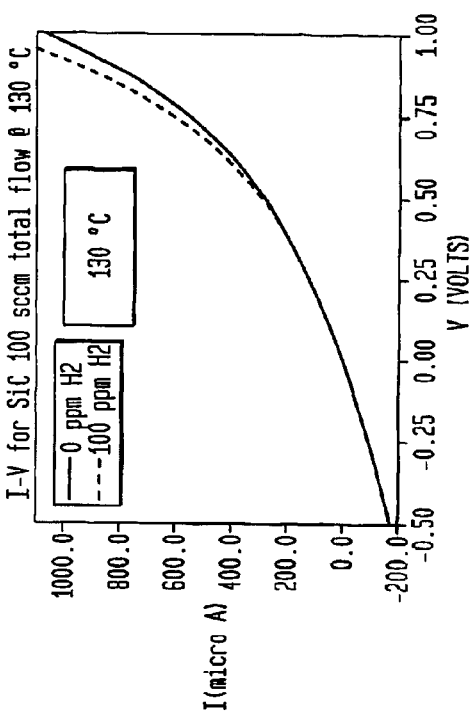
Figure 11D:
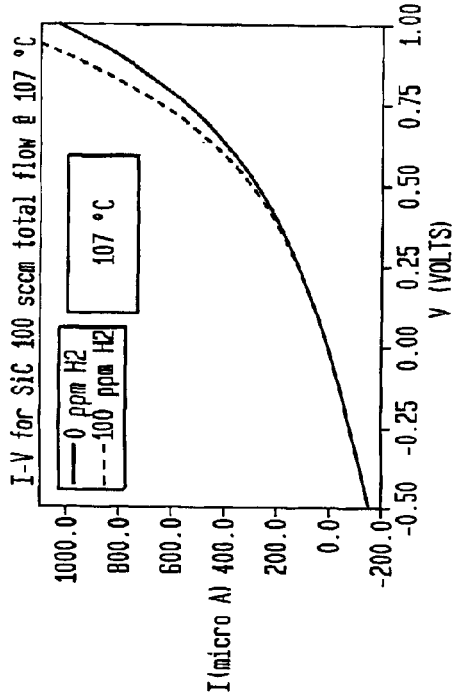
Figure 11E:
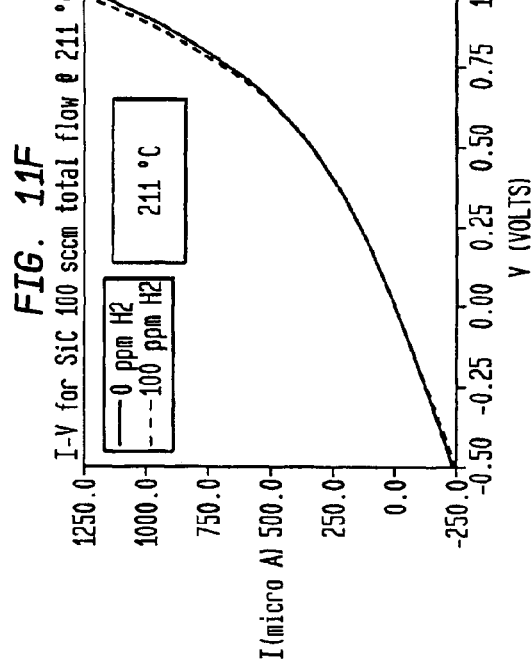
Figure 11F:
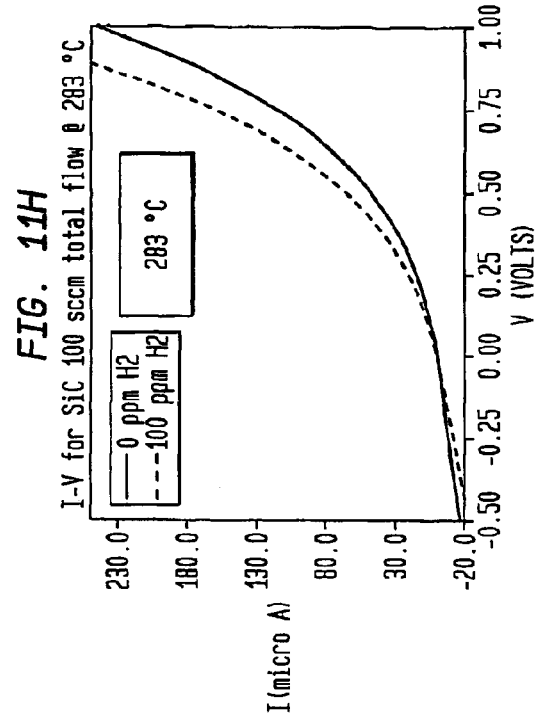
Figure 11G:
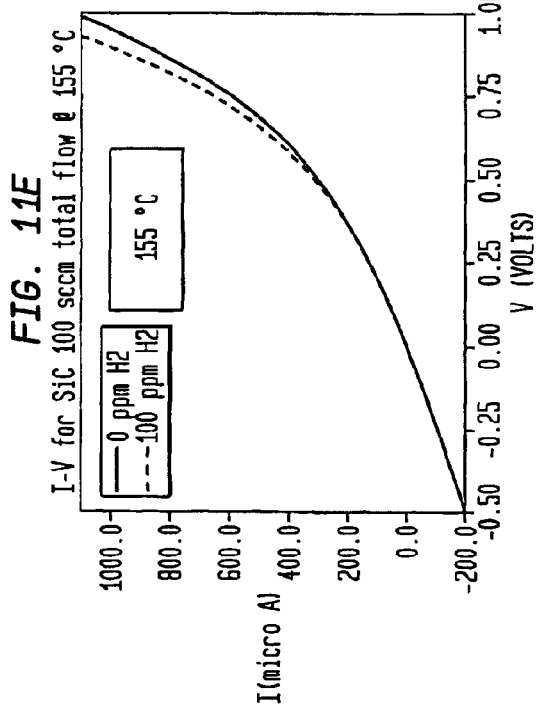
Figure 11H:
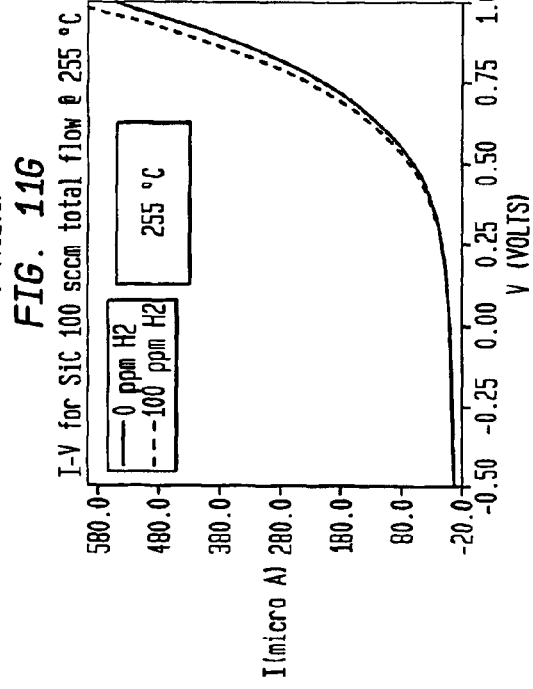

FIGS. 11A–H are graphical representations of the current versus voltage (I-V) response of a SiC-based device, specifically Device No. 5 on Table 2, to the presence of hydrogen (100 sccm total flows) measured at constant temperatures, respectively from A to H: 19° C., 47° C., 107° C., 130° C., 155° C., 211° C., 255° C., and 283° C. The rectifying character of the structure is evident. A hydrogen response is also evident by the large shift in the forward current with the addition of 100 ppm hydrogen to the flow. The SiC-based devices can be operated at much higher temperatures than the Si-based devices, but still show a useful response at room temperature as illustrated in FIG. 11A.

Figure 12:
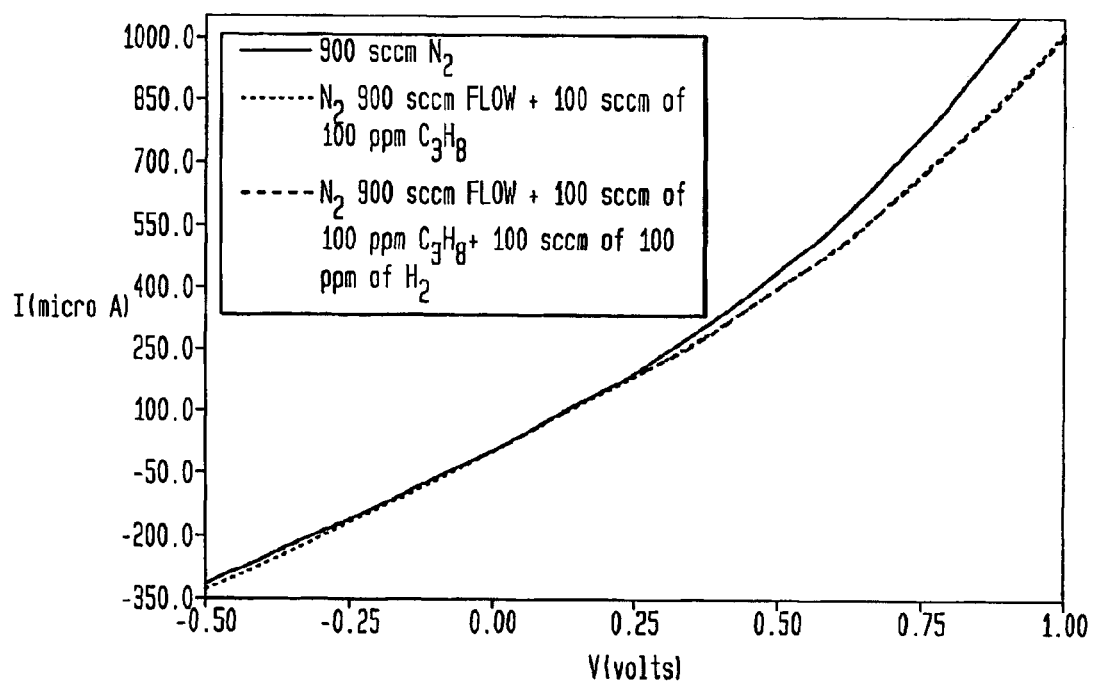
FIG. 12 is a graphical representation of an I-V curve for the Pd/AlN/SiC device demonstrating the response of this device to hydrogen in the presence of another gas, specifically, propane at a high temperature.

FIG. 12 is a graphical representation of an I-V curve for the Pd/AlN/SiC device demonstrating the response to hydrogen in the presence of propane at a high temperature (comparable to the response of the Pd/AlN/Si device shown in FIG. 10). Similar responses in the presence of oxygen and carbon monoxide (not shown), demonstrated the hydrogen selectivity of the Si—C devices in accordance with the present invention. The sensitivity of the SiC-based device at an applied voltage of 0.9 V was measured as a current shift of 100 μA for a 100 ppm addition of hydrogen to a 100 sccm flow of nitrogen as shown in FIG. 12. This sensitivity can be enhanced by using a larger voltage. Of course, the application of voltage is limited by the heat dissipation ability of the device. In addition, the sensitivity of the SiC-based device can be enhanced by increasing the flow rate of sample gas. Data suggests that the sensitivity of the device to hydrogen can be increased to 1 ppm by increasing the flow rate to 1000 sccm.

Figure 13:
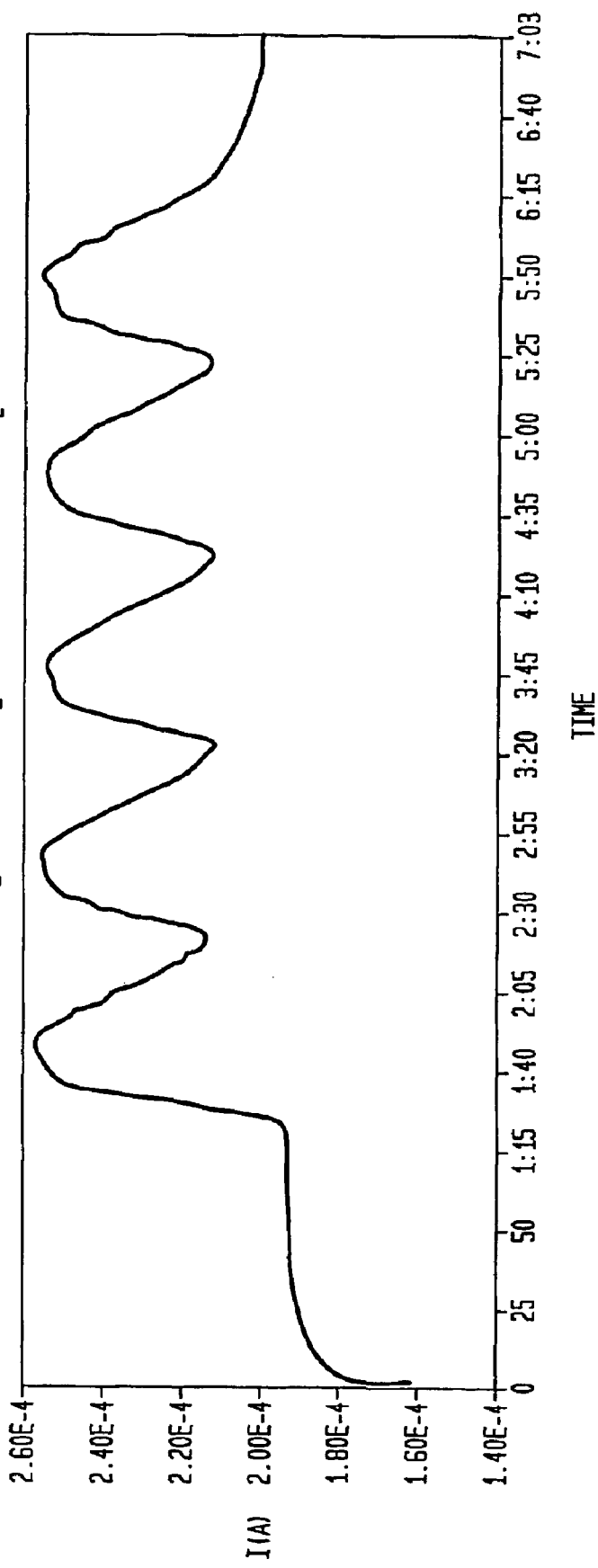
FIG. 13 is a graphical representation of the change in current (microamps) at a constant gate voltage with respect to time (sec) for the Pd/AlN/SiC sensor when subjected to a periodic alteration in the gas composition impinging on the sensor.

FIG. 13 is a graphical representation of the change in current (microamps) at constant gate voltage over time (sec) for a Pd/AlN/SiC sensor (Table 2, Device 5) when subjected to a periodic alteration in gas composition impinging on the sensor from 100 sccm of pure nitrogen to 100 sccm of 100 ppm hydrogen in nitrogen at a constant temperature of 293° C. This data shows that the sensor rapidly responds to the presence of hydrogen.

Figure 14:
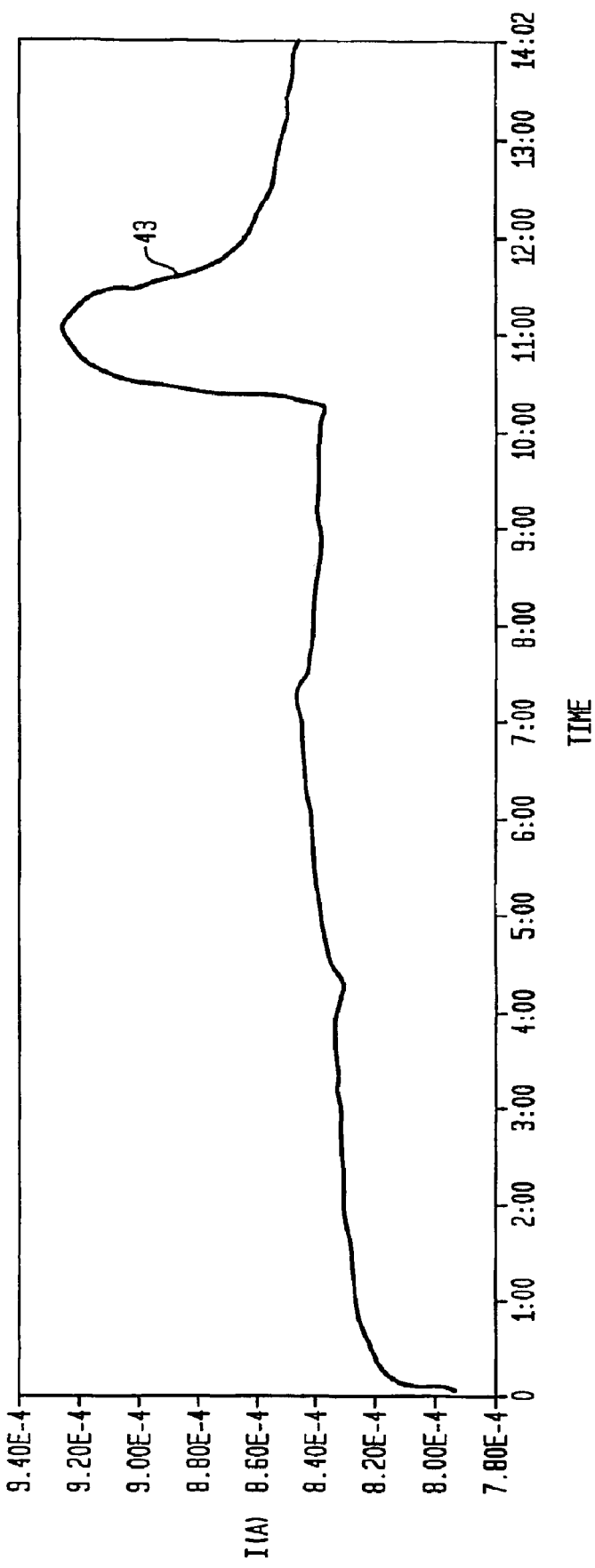
FIG. 14 is a graph of current, in microamps, measured as a function of time at a constant temperature (262° C.) for the Pd/AlN/SiC sensor when subjected to a constant 100 sccm flow of feed gas of varying composition.

FIG. 14 illustrates graphically the selectivity and response of a SiC-base device to 100 ppm hydrogen in feed gas of varying composition. The response of the device was measured in current (microamps) as a function of time at a constant temperature (262° C.) in a constant 100 sccm flow of feed gas. The composition of the gas was varied according to the following schedule: at t=0, 100 ppm $O_2$; at t=4 minutes, 100 ppm $C_3H_8$; at t=7 minutes, the $C_3H_8$ gas was shut off, at t=10 minutes, 100 ppm $H_2$; and a t=11 minutes, the $H_2$ was shut off. Curve 43 clearly shows the marked response to $H_2$. Similar tests were conducted with, $O_2$ and CO in the feed gas, and similar results were obtained.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. A device for the detection of hydrogen gas, comprising:

a semiconductor substrate having a thickness of approximately between 360 Å to 400 Å;

an epitaxial layer of AlN having a thickness of approximately between 500 Å to 5000 Å disposed on a face surface of the semiconductor substrate as an insulating layer; and a metal electrode formed of palladium disposed on the insulating layer, the metal electrode having a thickness of approximately between 1000 Å and 2000 Å, and being a catalyst for hydrogen diffusion, whereby the hydrogen gas is detected in response to a variation in a capacitance characteristic.

2. The device of claim 1 wherein the metal electrode is selected from the group consisting of platinum, rhodium, and alloys thereof.

3. The device of claim 2 wherein the metal electrode is formed of an alloy of palladium.

4. The device of claim 1 wherein the semiconductor substrate is silicon.

5. The device of claim 1 wherein the semiconductor substrate is silicon carbide.

6. The device of claim 5 wherein the silicon carbide substrate is 6H-SiC.

* * * * *